United States Patent
Redl et al.

(10) Patent No.: US 9,179,898 B2
(45) Date of Patent: Nov. 10, 2015

(54) TISSUE SEALING SYSTEM AND APPARATUS

(75) Inventors: Heinz Redl, Vienna (AT); Zafar Khakpour, Vienna (AT); Rene Fortelny, Weidling (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1094 days.

(21) Appl. No.: 12/650,185

(22) Filed: Dec. 30, 2009

(65) Prior Publication Data

US 2010/0168779 A1  Jul. 1, 2010

Related U.S. Application Data

(60) Provisional application No. 61/141,437, filed on Dec. 30, 2008.

(51) Int. Cl.
*A61B 17/34* (2006.01)
*A61B 17/00* (2006.01)

(52) U.S. Cl.
CPC ....... *A61B 17/00491* (2013.01); *A61B 17/3474* (2013.01); *A61B 2017/00495* (2013.01); *A61B 2017/00522* (2013.01)

(58) Field of Classification Search
CPC ............... A61B 17/00491; A61B 2017/00495; A61B 17/3474; A61B 2017/00522
USPC ......... 606/185, 214; 604/23, 24, 26; 137/594; 251/149.1
See application file for complete search history.

(56) References Cited

U.S. PATENT DOCUMENTS

| 5,665,067 A | 9/1997 | Linder et al. |
| 5,810,885 A | 9/1998 | Zinger |
| 6,328,229 B1 | 12/2001 | Duronio et al. |
| 6,745,738 B1 * | 6/2004 | Bosscher ................... 123/90.65 |

(Continued)

FOREIGN PATENT DOCUMENTS

| EP | 2000215 A2 | 12/2008 |
| JP | 05168714 A | 7/1993 |

(Continued)

OTHER PUBLICATIONS

International Search Report and Written Opinion for corresponding International Application No. PCT/US2009/069837, dated Jun. 2, 2010.

*Primary Examiner* — Kathleen Holwerda
*Assistant Examiner* — Sarah Simpson
(74) *Attorney, Agent, or Firm* — Greer, Burns & Crain, Ltd.

(57) ABSTRACT

A laparoscopic tissue sealant spray apparatus and system having a laparoscopic tissue sealant spray assembly combined with a trocar assembly, the tissue sealant spray assembly having an elongate delivery tube. A spray outlet at a distal end of the elongate delivery tube may be rounded or angled. A ring member provided at the distal end of the elongate delivery tube directs a spray cone toward a portion of a target tissue site, and the spray cone may be repositioned to a different portion of the target tissue site by rotation of the elongate delivery tube. The trocar assembly includes a vent opening that connects to a venting valve member that provides a vent path which passively opens upon operation of the tissue sealant spray assembly, avoiding excessive pressure build-up within a body cavity.

5 Claims, 3 Drawing Sheets

(56) References Cited

U.S. PATENT DOCUMENTS

| | | |
|---|---|---|
| 6,802,822 B1 | 10/2004 | Dodge |
| 7,000,894 B2 * | 2/2006 | Olson et al. ............... 251/149.1 |
| 7,537,174 B2 | 5/2009 | Redl et al. |
| 8,394,080 B2 * | 3/2013 | Jepson et al. ............... 604/537 |
| 2004/0059283 A1 * | 3/2004 | Kirwan et al. ............... 604/23 |
| 2005/0113797 A1 * | 5/2005 | Ott et al. ............... 604/506 |
| 2007/0005007 A1 * | 1/2007 | Hoogenakker et al. ......... 604/82 |
| 2008/0035221 A1 * | 2/2008 | Gawryjolek ............... 137/613 |

FOREIGN PATENT DOCUMENTS

| | | |
|---|---|---|
| WO | WO-00/09199 A1 | 2/2000 |
| WO | WO-2006/076427 A2 | 7/2006 |

* cited by examiner

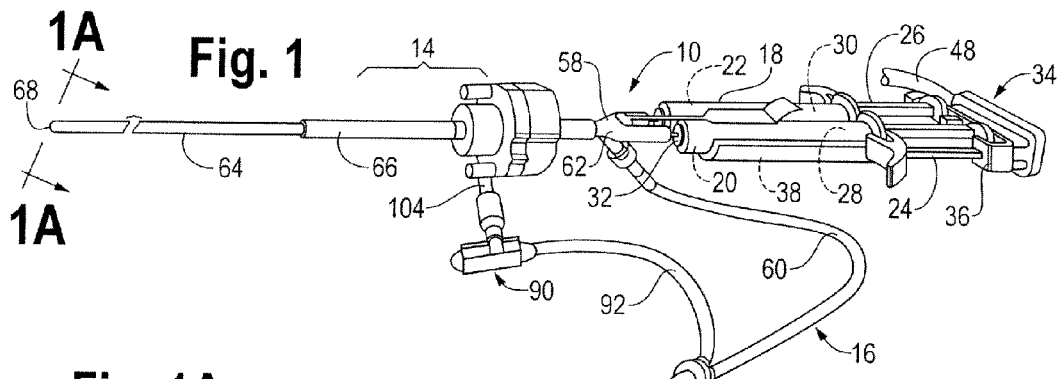
Fig. 1
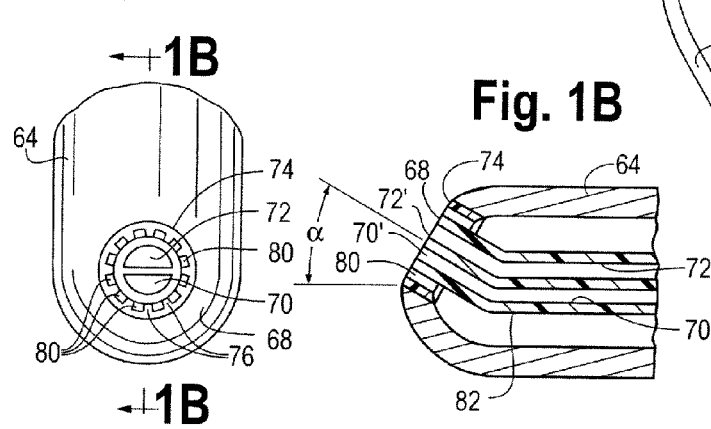
Fig. 1A
Fig. 1B
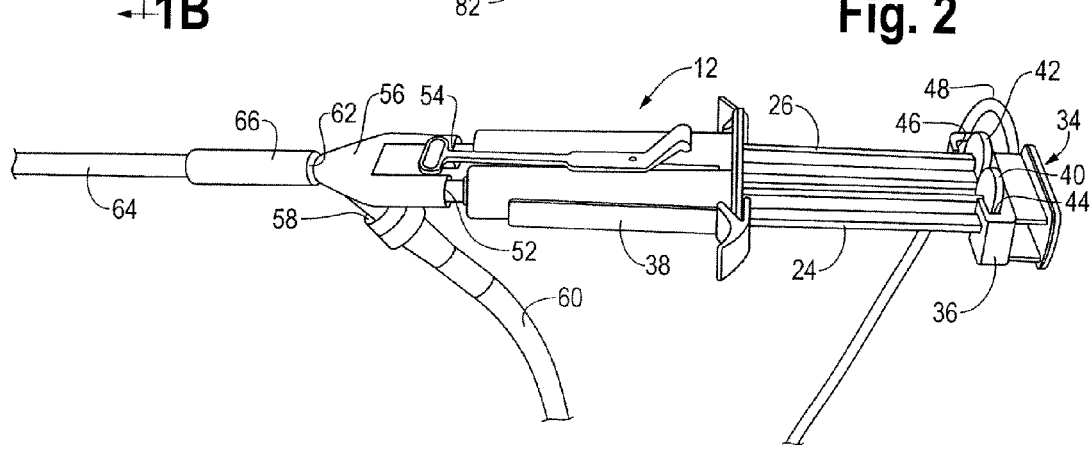
Fig. 2
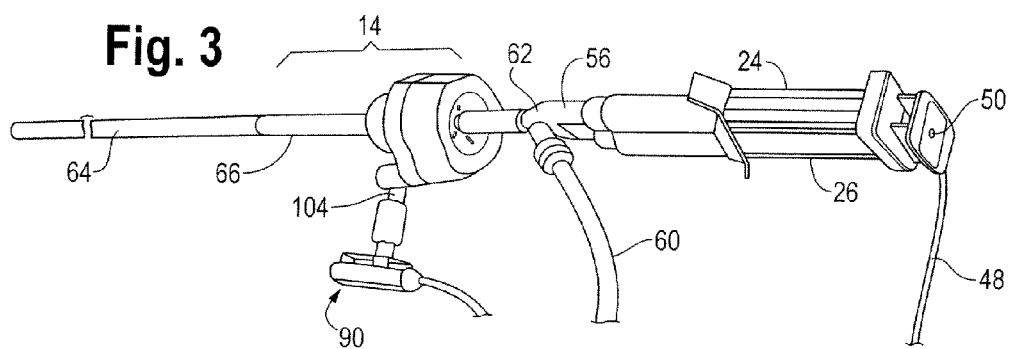
Fig. 3

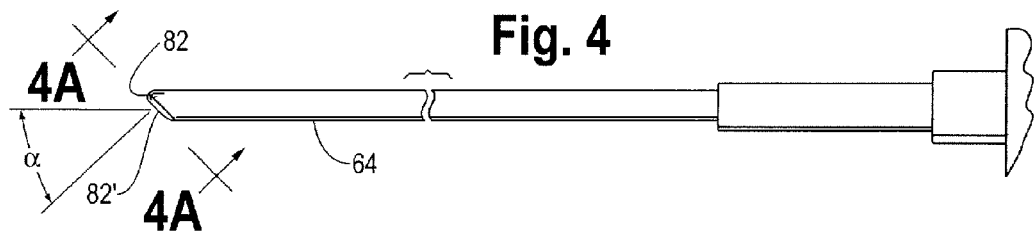
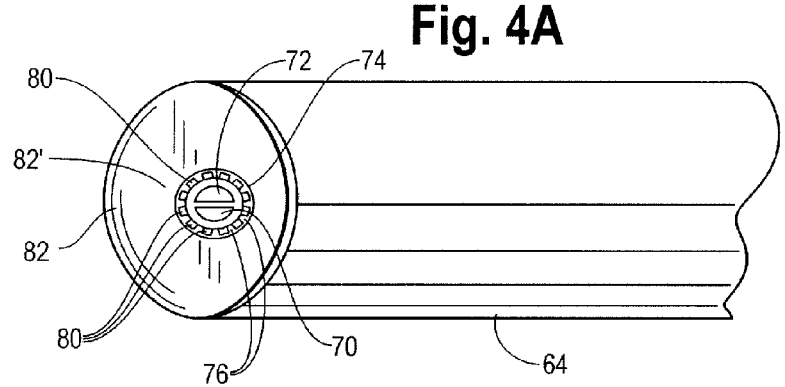
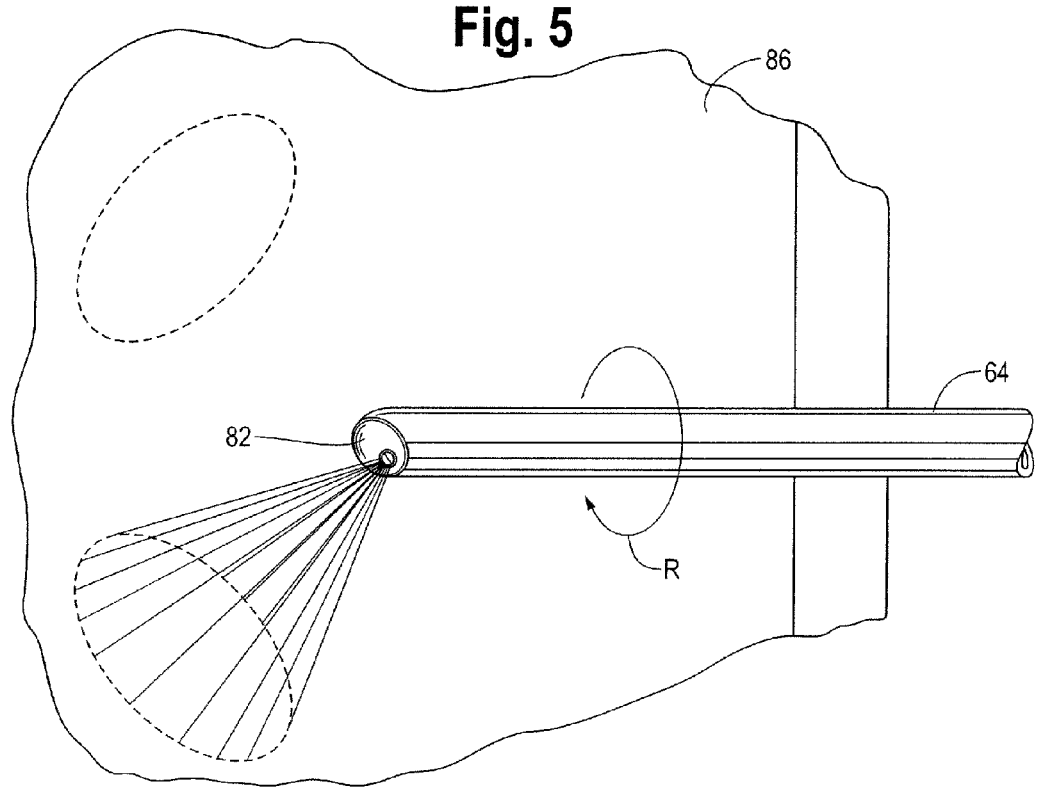

TISSUE SEALING SYSTEM AND APPARATUS

REFERENCE TO RELATED APPLICATIONS

This application claims the benefit of the filing date of U.S. Provisional Application No. 61/141,437, filed Dec. 31, 2008, the disclosure of which is incorporated herein by reference.

BACKGROUND

1. Filed of the Disclosure

This disclosure is generally directed to systems for applying a sealant to a work surface and, more particularly, to an apparatus and system for applying tissue sealant to biological tissue employing structure that facilitates controlled spray application of tissue sealant and passive control of gas pressure.

2. Description of the Related Art

Various apparatus and systems have been disclosed for application of tissue sealants. One such disclosure is U.S. Pat. No. 7,537,174, entitled "Hand Triggered Tissue Sealant Spray Apparatus and System," the entirety of which is incorporated herein by reference. An effective tissue sealant is a two-component tissue sealant made up of fibrinogen and thrombin. Because these two components react quickly with one another to cause clotting, it is desirable to isolate the two components from one another for as long as possible, until they are sprayed onto a target tissue site, such as a bodily organ.

A trocar device, which is known for use in laparoscopic surgical procedures, may be employed with an elongate delivery tube to deliver the two components, e.g., fibrinogen and thrombin, from a double-barrel syringe to a target tissue site. In order to spray the components of the tissue sealant onto a target tissue site, gas is introduced, such as through a Y-shaped spray adapter, as described in the aforementioned U.S. Pat. No. 7,537,174.

While such tissue sealing systems have been described and used, these systems limit the ability of the surgeon to direct the spray. With existing laparoscopically-introduced tissue spray systems, the surgeon can apply tissue sealant to a particular portion of a target tissue site, but then needs to withdraw the delivery tube at least partially into, or completely from, the trocar, reposition the delivery tube, then apply more tissue sealant to another portion of the target tissue site. This interrupted application of tissue sealant undesirably increases procedure time.

Another disadvantage of existing gas driven tissue delivery systems is the need for the surgeon or other medical professionals to carefully monitor the gas pressure introduced via the trocar to a bodily cavity. To perform most endoscopic, and in particular, laparoscopic procedures, the abdomen or other bodily cavity is filled with $CO_2$ gas, controlled by a special controller device where the pressure range is preset and maintained by monitoring, automatically delivering more $CO_2$ gas as needed. With certain newer controller devices, the release of gas from the bodily cavity may also be controlled. With such gas driven tissue delivery systems, an unacceptable increase of intracavity pressure may be realized if no venting is performed. In order not to overdistend the abdomen or other bodily cavity, and to avoid excessive pressure increase, the amount of gas employed for spraying should be limited. Moreover, the pressure on the surface of the target tissue to be sprayed should not exceed the pressure in small blood vessels, so as to avoid a gas embolism in the vasculature.

Venting can be accomplished by the surgeon by opening of a manually-operated valve at the trocar. Alternately, certain newer laparoscopic gas controller devices can actively control the supply of gas introduced into, or released from, the bodily cavity. However, these solutions require nearly-constant monitoring of intracavity pressure and pressure of gas, such as $CO_2$ or helium, used in the spray device or otherwise introduced into the bodily cavity.

It would therefore be desirable to provide a laparoscopic tissue sealant spray delivery system and apparatus that speeds up procedure time and reduces the need for monitoring of the pressure of gas introduced into the bodily cavity, thereby permitting the surgeon or other medical professionals to pay more attention to other matters relating to the procedure.

SUMMARY OF THE DISCLOSURE

Various embodiments of a laparoscopic tissue sealant spray delivery system and apparatus are described below. In one embodiment, the laparoscopic tissue sealant spray assembly is provided with an elongate delivery tube having a rounded distal end. In another embodiment, the elongate delivery tube is provided with an angled end, such as in a range of 30° to 45°. In either of these embodiments, the elongate delivery tube is preferably provided with separate passageways, one for each component of a two component fluid, such as a tissue sealant, and these separate sealant component passageways are surrounded by a gas passageway. The sealant component passageways and the gas passageway terminate at a ring member provided at the distal end of the elongate delivery tube, with the ring member having a plurality of teeth projecting radially inwardly from an inner diameter thereof.

The inner diameter of the ring member, the teeth, and an outer wall of the sealant component passageways define a plurality of apertures at the distal end of the elongate delivery tube for gas in the passageway to first be exposed to the two components as the components are simultaneously ejected from the elongate delivery tube, thereby spraying the tissue sealant onto a target tissue site. The rounded or angled distal end may be easily repositioned by simply rotating the elongate delivery tube to direct a conical spray of tissue sealant to a different portion of a target tissue site.

Another aspect of the present disclosure is a venting valve member provided at a vent opening of a trocar assembly of the laparoscopic tissue sealant spray apparatus and system. The venting valve member has a gas inlet in fluid communication with a gas passageway branched off from the gas supply passageway that delivers gas to the tissue sealant spray assembly. A valve within the venting valve member is biased by a spring in the direction of the gas inlet, closing a vent path within the venting valve member. When the tissue sealant spray system is in operation, pressurized gas entering the gas inlet of the venting valve member urges the valve therein against the spring, thereby opening the vent path and permitting gas to be vented from a bodily cavity, through a trocar tube and vent opening of the trocar assembly, and out through the venting valve member.

The venting valve member includes a movable valve rod having a first axially-extending section of a diameter sufficient to block the vent path, and a second axially-extending section of a smaller diameter, permitting gas to pass through the vent path, around the second axially-extending section of the valve rod. The first axially-extending section of the valve rod may include a hollowed interior cavity to accommodate the spring that biases the valve rod toward a sealed condition in which the first axially-extending section closes the vent path. The second axially-extending section includes an end cap in sealed communication with an interior of a valve conduit within the venting valve member, thereby permitting gas pressure from the pressurized gas P to build up and exert a force sufficient to overcome the biasing force of the spring. The sealed communication also serves to isolate the pressurized gas employed to actuate the valve rod from the gas being vented from the bodily cavity. The venting valve member significantly diminishes gas build-up within the bodily cavity during the laparoscopic tissue spray procedure. These and other aspects of the present disclosure will now be described in more detail, with reference to the following drawings.

BRIEF DESCRIPTION OF THE SEVERAL VIEWS OF THE DRAWINGS

FIG. 1 is a perspective view of a laparoscopic tissue sealant spray apparatus and system of a first embodiment of the present disclosure;

FIG. 1A is an enlarged end view of a portion of the laparoscopic tissue sealant spray apparatus and system of FIG. 1, taken along lines 1A-1A of FIG. 1, showing the distal end of an elongate delivery tube surrounded by a trocar;

FIG. 1B is a cross-sectional view of the distal end of the elongate delivery tube of FIG. 1A, taken along lines 1B-1B of FIG. 1A;

FIG. 2 is a perspective view of a laparoscopic tissue sealant spray assembly with an elongate delivery tube, partially broken away, and prior to insertion into a trocar assembly;

FIG. 3 is a perspective view of the laparoscopic tissue sealant spray assembly of FIG. 2, in combination with a trocar assembly having a venting valve member of the present disclosure provided on a valve opening of the trocar assembly;

FIG. 4 is a plan view of an elongate delivery tube of a laparoscopic tissue sealant spray apparatus of the first embodiment of the present disclosure, with a segment of the elongate delivery tube and most of the laparoscopic tissue sealant spray assembly broken away for clarity;

FIG. 4A is an end view of the elongate delivery tube shown in FIG. 4, taken along the lines 4A-4A of FIG. 4;

FIG. 5 is an environmental view of a bodily cavity, showing the distal end portion of the elongate delivery tube shown in FIG. 4, illustrating the manner in which the elongate delivery tube of the laparoscopic tissue sealant spray apparatus of the first embodiment of the present disclosure may be manipulated within the bodily cavity and without being pulled back into the trocar in order to direct tissue sealant to distinct portions of a target site;

DETAILED DESCRIPTION OF THE PREFERRED EMBODIMENTS

Figure 6:
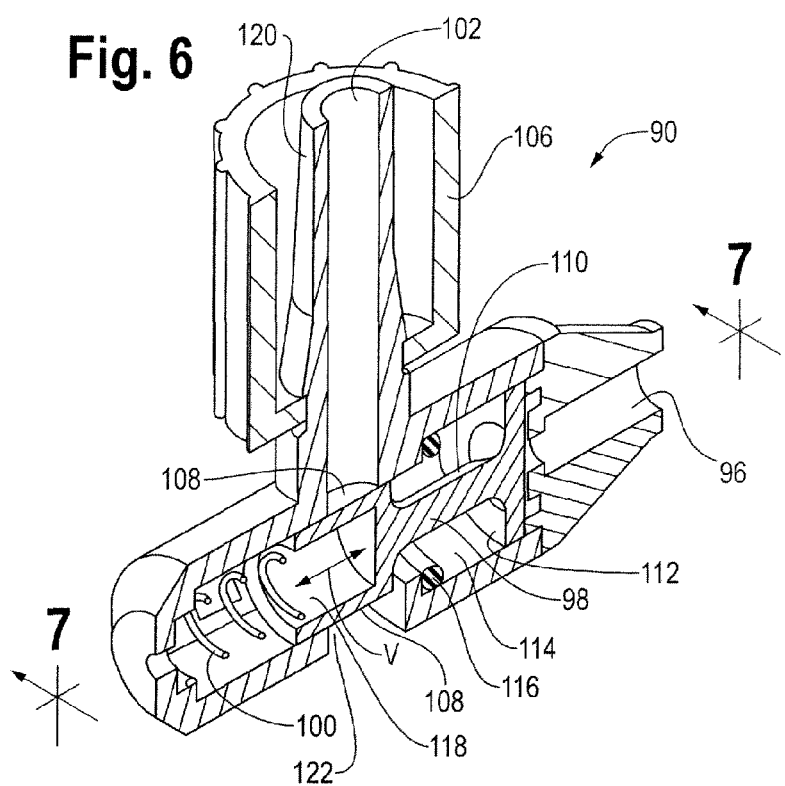
FIG. 6 is a perspective view, in cross-section, of a venting valve member of the present disclosure.

The laparoscopic tissue sealant spray apparatus and system 10 of the present disclosure includes a tissue sealant spray assembly 12, a trocar assembly 14, and a network of gas supply tubing 16. The tissue sealant spray assembly 12 has a barrel assembly 18 defining a compartment for a tissue sealant. The fluid to be delivered is preferably a tissue sealant, and is most preferably a multi-component tissue sealant, such as a two-component sealant including thrombin and fibrinogen. Much of the tissue sealant spray apparatus and system, up to and including a generally Y-shaped spray adapter member, may be as described in U.S. Pat. No. 7,537,174, wherein the components of the apparatus and system are described in greater detail than is provided here.

In the case of a two-component sealant where the components must be isolated from one another until their application to a target site, the barrel assembly 18 includes two interior bores 20, 22, with each component stored in one of the interior bores 20, 22. Pistons 24, 26 are movably positioned in each of the respective interior bores 20, 22. Each of the pistons 24, 26 is provided with a plunger member 28, 30 at the distal end thereof, each of the plunger members 28, 30 forming a seal with an inner wall of the respective interior bore 20, 22, such that advancement of the pistons 24, 26 toward a distal end 32 of the barrel assembly 18 ejects the components of the tissue sealant from the interior bores 20, 22.

In order to provide simultaneous ejection of the two components of the tissue sealant, a pusher member 34 that bridges both of the pistons 24, 26 is operatively associated with the pistons 24, 26. The pusher member 34 may be provided with a proximal platform 36 slidably attached to a frame 38. Each of the plunger members 28, 30 terminates in a flanged end 40, 42 received in a corresponding slot 44, 46 of the proximal platform 36.

A gas passageway 48 connects to the pusher member 34. An opening 50 on the proximal platform 36 is restricted as the user actuates the pusher member 34. This blockage of the opening 50 causes the gas pressure to increase to the static pressure of the gas and generates a supply signal to a gas supplying device (not shown). This signal operates a valve on the gas supplying device which in turn operatively supplies gas to the network of gas supply tubing 16. In an embodiment this gas may be carbon dioxide, but such gas may be any gas which is suitable for the application.

At the distal end 32 of the barrel assembly 18, each of the interior bores 20, 22 is in fluid communication with a respective tissue sealant inlet 52, 54 of a generally Y-shaped spray adapter member 56. The generally Y-shaped spray adapter member 56 also includes a gas inlet connection 58, to which a gas supply tube 60 that one branch of the network of supply tubing 16 connects. Thus activation of the valve on the gas supplying device by selective blockage of the opening 50 provides a flow of gas into the network 16 and thereby the supply tubing 16 and such gas flows into the gas inlet connection 58 of the Y-shaped adapter member 56.

Elongate Delivery Tube

The generally Y-shaped spray adapter member 56 is provided with a connection outlet 62 in fluid communication with both the gas inlet connection 58 and the tissue sealant inlets 52, 54. The connection outlet 62 is in fluid communication with an elongate delivery tube 64, which extends through a trocar tube 66 of the trocar assembly 14.

In the embodiment shown in FIGS. 1, 1A and 1B, a spray outlet 68 at the distal end of the elongate delivery tube 64 is rounded. The elongate delivery tube 64 defines a conduit therein with separate sealant component passageways 70, 72, one for each of the tissue sealant components. A ring member 74 having a plurality of teeth 76 projecting radially inwardly is provided at the rounded spray outlet 68 at the distal end of the elongate delivery tube 64. The elongate delivery tube 64 also includes a gas passageway 78 in fluid communication with the connection outlet 62 of the generally Y-shaped spray adapter member 56. The gas passageway 78 surrounds the sealant component passageways 70, 72 and terminates at the rounded spray outlet 68 at the distal end of the elongate delivery tube 64. Gas in the gas passageway 78 is able to pass through the rounded spray outlet 68 of the elongate delivery tube 64 via apertures 80 defined by the teeth 76, the inner diameter of the ring 74, and an exterior wall 82 of the sealant component passageways 70, 72.

The connection between the generally Y-shaped spray adapter member 56 and the elongate delivery tube 64 is such that gas from the gas supply tube 60 enters the gas inlet connection 58 of the generally Y-shaped spray adapter member 56, but rather than mixing with the tissue sealant components in the spray adapter member 56, the gas remains isolated from the components, and the components remain isolated from one another, down the entire length of the elongate delivery tube 64. The gas is only exposed to the tissue sealant components at the spray outlet 68, simultaneously with the tissue sealant components first being exposed to one another, when the gas passes through the apertures 80. Distributing gas delivery via a plurality of apertures 80, as is achieved with the ring member 74, advantageously significantly reduces the pressure and flow rate of the gas necessary to achieve the desired spray mixing of the components as the mixed components are applied at the target tissue surface. The present design also reduces gas volume which is emitted from the delivery tube compared to existing laparoscopic spray systems, and results in amore defined spray cone diameter, enabling more precision in the location of sealant application.

The ring member 74 and the openings 70', 72' at the distal end of the separate sealant component passageways 70, 72 are preferably displaced slightly from the rounded distal end 68 and inclined at an angle α in the range of 30°-45° relative to again axis of the elongate delivery tube, and inclined preferably at a 45° angle. By so positioning the ring member 74, the spray cone may be easily re-directed during operation of the laparoscopic tissue sealant spray apparatus and system 10, by simply rotating the elongate delivery tube 64. Moreover as the openings 70', 72' are displaced slightly from the spray outlet 68 the spray outlet 68 forms a smooth surface that upon contacting the tissue of a patient provides a touch control to the surgeon without irritating the tissue. In addition, when the spray outlet 68 is in contact with the patient tissue, the displacement of the openings 70', 72' prevents the tissue from blocking the openings thereby lessening the potential for clogs.

Turning to FIGS. 4, 4A and 5, the laparoscopic tissue sealant spray apparatus and system is substantially the same as in the previous embodiment, but the rounded spray outlet 82 at the distal end of the elongate delivery tube 64 includes an angled portion 82' that extends at least short distance beyond an outer perimeter of the ring member 74.

As illustrated in FIG. 5, a benefit of the angled portion of the rounded spray outlet 82 is that the spray cone 84 formed when the gas disperses the combined tissue sealant components may be redirected within a bodily cavity 86 from a first portion of a target tissue site to a second portion of the target tissue site by simply manipulating the elongate delivery tube 64 by rotation, as indicated by the directional arrow R. As is the case with the elongate delivery tube 64 illustrated in FIGS. 1, 1A and 1B, a ring member 74 is provided in the spray outlet 82, having teeth 76 projecting radially-inwardly from an inner diameter of the ring member 74, defining a plurality of apertures 80 for gas to eject from the gas passageway within the elongate delivery tube 64 surrounding the separate passageways 70, 72 for the tissue sealant components.

Venting Valve Member

Figure 7:
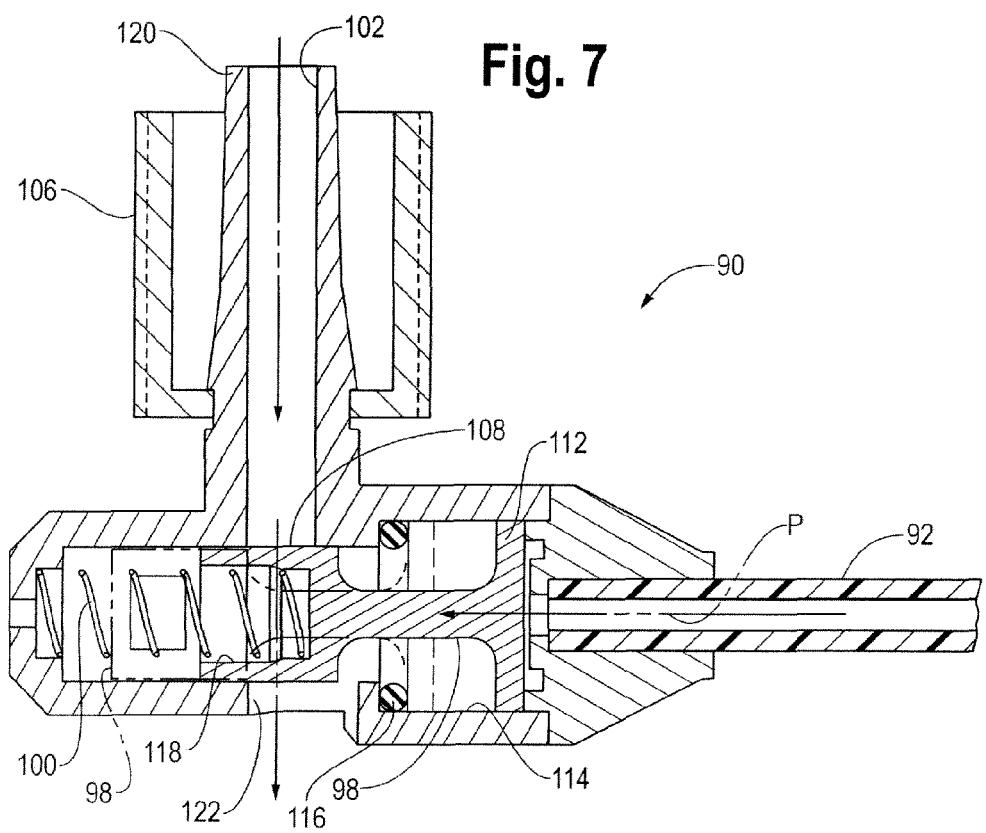
FIG. 7 is a plan view of the venting valve member of FIG. 6, taken along directional lines 7-7 of FIG. 6.

Referring to FIGS. 1 and 3 in conjunction with FIGS. 6 and 7, a venting valve member 90 is connected to a gas passageway 92 of the network of supply tubing 16. The gas passageway 92 and the gas supply tube 60 branch off from a main gas tube 94 at a connector 97. The gas passageway 92 is secured to a gas connecting end 96 of the venting valve member 90. The venting valve member 90 includes a movable valve rod 98 biased by a spring 100 in a direction toward the gas connecting end 96 and a vent path 102 in fluid communication with a valve opening 104 of the trocar assembly 14. The vent path 102 is selectively opened by gas pressure P from the gas passageway 90 urging the valve rod 98 against the restoring force of the spring 100, as indicated by the arrow V in FIG. 7. FIG. 7 also illustrates in phantom lines the position of the valve rod 98 when displaced by the gas pressure P, against the spring 100, to the position in which the vent path 102 is open.

The vent path 102 is selectively opened by gas pressure P from the gas passageway 90 urging the valve rod 98 against the spring 100, as indicated by the arrow V in FIG. 6. FIG. 7 also illustrates in phantom lines the position of the valve rod 98 when displaced by the gas pressure P, against the spring 100, to the position in which the vent path 102 is open. The geometry of the valve rod 98 of the venting valve member 90 is such that a first axially-extending section 108 is of a sufficient diameter to block the vent path 102 when the valve rod 98 is in the closed position, as illustrated in solid lines in FIG. 7. A second axially-extending section 110 of the valve rod 98 has a narrower diameter than the first axially-extending section, such that when the valve rod 98 is actuated by gas pressure P from the gas passageway 90, gas may be vented through the vent path 102, around the second axially-extending section.

The second axially-extending section 110 of the valve rod 98 terminates at a solid end cap 112 opposite the first axially-extending section 108. The end cap 112 is in sealed, yet axially-movable, communication with a valve conduit 114 within the venting valve member 90 in which the valve rod 98 is seated. This sealed engagement permits gas pressure from the pressurized gas P to build up and exert a force sufficient to overcome the biasing force of the spring, and isolates pressurized gas P from the gas passageway from gas in the bodily cavity being vented through the vent path 102. The end cap 112 also serves to limit the travel of the valve rod 98. As illustrated in FIGS. 6 and 7, the valve conduit 114 is stepped radially inwardly (from right-to-left in the drawing figures), from a first inner diameter approximately equal to an outer diameter of the end cap 112, to a second inner diameter that is less than the outer diameter of the end cap 112, but large enough to accommodate the first axially-extending section 108 of the valve rod 98. A gasket 116, such as an O-ring, is preferably provided at an end of the first inner diameter region of the valve conduit 114 adjacent the step radially inwardly to the second inner diameter region. The gasket 116 dampens vibrations and reduces noise resulting from impact between the end cap 112 and the stepped portion of the valve conduit 114 as the pressurized gas P forces the valve rod 98 against the spring 100.

The first axially-extending section 108 of the valve rod 98 preferably includes a hollowed interior cavity 118 to accommodate a portion of the spring 100.

When, as described previously, the opening 50 (FIG. 3) is blocked to signal the gas delivery device (not shown) to supply gas under pressure to the supply tubing 16 (and therefore the gas inlet connection 58), this flow of gas also pressurizes the gas within the gas passageway 92. This gas pressure within the gas passageway 92 forms pressure P within the gas connecting end 96, which urges the valve rod 98 against the restoring force of the spring 100, thereby opening the vent path 102. This opening of the vent path 102 thereby coincides with the supply of gas through the Y-shaped adapter member 56, gas passageway 78 and apertures 80 into the patient. This allows for the selective venting or evacuation of this volume of gas from the bodily cavity (e.g., the abdominal cavity), as it is being supplied, through the trocar tube 66 and the valve opening 104 of the trocar assembly 14, and to the atmosphere, with the end result being very minimal net pressure increase or increase in volume of gas in the patient's cavity, during continuous spraying of tissue sealant. When the opening 50 is uncovered, spraying is stopped, gas flow into the patient is interrupted, and the gas pressure P ceases to be supplied to the gas connecting end 96 of the venting valve member 90, upon which the valve rod 98 of the venting valve member 90 is closed by the restoring force of the spring 100.

The vent path 102 of the venting valve member 90 may be secured to the valve opening 104 of the trocar assembly by a locking member 106, which may be internally threaded and may engage external threads (not shown) on the valve opening 104 of the trocar assembly 14. In an embodiment this locking member 106 and valve opening 104 may be formed as a standard luer fitting. A vent path connector end 120 is configured to attach to a vent outlet at the valve opening 104 of the trocar assembly, the vent path 102 being in fluid communication with the vent path connector end 120. The venting valve member 90 further includes a vent opening 122 at a terminus of the vent path 102 and in fluid communication with the second inner diameter region of the valve conduit 114.

While various aspects of the present disclosure have been described, it will be understood by those of ordinary skill in the art that variations may be made thereto that are still within the scope of the appended claims.

What is claimed is:

1. An improved tissue sealant applicator having a barrel assembly containing a multi-component tissue sealant, a piston movably positioned in a proximal end of the barrel assembly, and an elongate delivery tube, in combination with a trocar assembly having a trocar tube for introducing the elongate delivery tube into a bodily cavity, the improvement comprising:
   a spray adapter member having
   a gas inlet connection;
   a distinct chamber for each component of the multi-component tissue sealant;
   a tissue sealant inlet in fluid communication with both the gas inlet connection and a distal end of the barrel assembly; and
   a connector outlet in fluid communication with both the gas inlet connection and the tissue sealant inlet;
   the elongate delivery tube having a proximal end connected to the connector outlet of the spray adapter member, the distinct chamber for each component of the multi-component tissue sealant and a spray outlet at an opposite distal end, the elongate delivery tube received in the trocar tube of the trocar assembly, with the spray outlet at the distal end of the elongate delivery tube exposed and the elongate delivery tube being rotatable relative to the trocar tube; and
   a venting valve assembly having a biased movable valve rod slidably located within the venting valve assembly, and configured to provide a seal within a vent path associated with the venting valve assembly and in fluid communication with a vent opening disposed at a terminus of the vent path opposite the trocar assembly, the vent opening configured for allowing gas to pass from the vent path to atmosphere by selectively opening the vent path under the action of the valve rod by gas pressure;
   wherein a vent path connector associated with the trocar assembly defines a first gas passageway to the venting valve assembly, and a valve conduit in fluid communication with a gas supply tube defines a separate second gas passageway from the venting valve assembly, such that the gas from the trocar assembly passes from the vent path to atmosphere by selective gas pressure actuation of the valve rod.

2. The improved tissue sealant applicator of claim 1, wherein the elongate delivery tube further includes a third gas passageway in fluid communication with the connector outlet of the spray adapter member, the third gas passageway of the elongate delivery tube having a separate passageway for each component of the multi-component tissue sealant, and the third gas passageway and the separate passageway for each component of the multi-component tissue sealant terminating at the distal end of the elongate delivery tube at a ring member having a plurality of teeth projecting radially inwardly from an inner diameter of the ring, the teeth extending across an outlet end of the third gas passageway and around an outer wall of the separate passageway, whereby the outer wall of the separate passageway, the teeth, and the inner diameter of the ring member define a plurality of apertures in the distal end of the elongate delivery tube.

3. The improved tissue sealant applicator of claim 1, wherein the vent path connector is attached to the trocar assembly, and defines the first gas passageway to the venting valve assembly, and the valve conduit is attached to the gas supply tube, and defines the separate second gas passageway to the venting valve assembly, such that the gas from the trocar assembly passes from the vent path to atmosphere by selectively opening the first gas passageway when the valve rod is actuated by the gas pressure delivered from the separate second gas passageway.

4. An improved tissue sealant spray applicator for applying a multiple component fluid into a bodily cavity through a trocar assembly extending into the bodily cavity, the multiple component fluid being contained within a multiple component assembly having a barrel assembly containing the multi-component fluid, the barrel assembly including a distinct chamber for each of the components, a piston movably positioned in a proximal end of the barrel assembly, the trocar assembly having a trocar tube for introducing an elongate delivery tube into the bodily cavity, a vent outlet and forming a vent passageway for placing the vent outlet in fluid communication with the bodily cavity, the improvement comprising:
   a spray adapter member having
   a gas inlet connection;
   a plurality of fluid inlets, with at least one of the fluid inlets in corresponding fluid communication with one of the chambers; and
   an adapter member outlet in fluid communication with the gas inlet connection and the plurality of fluid inlets;
   the elongate delivery tube having a proximal end connected to the adapter member outlet of the spray adapter member, an opposite distal end region forming a spray outlet in fluid communication with the gas inlet connection and the plurality of fluid inlets, the elongate delivery tube received in the trocar tube of the trocar assembly, and sized to extend through the trocar tube with the distal end region of the elongate delivery tube exposed and the elongate delivery tube being rotatable relative to the trocar tube;
   a main gas tube in fluid communication with the gas inlet connection;
   a gas supply tube in fluid communication with the main gas tube;
   a venting valve assembly including a gas connecting end attached to the gas supply tube, a valve conduit in fluid communication with the gas connecting end, a vent path connector end configured to attach to the vent outlet of the trocar assembly and a vent path in fluid communication with the vent path connector end, the venting valve assembly also including a biased movable valve rod slidably located within the valve conduit and configured to provide a seal within the vent path;

a vent opening, wherein the vent opening is in fluid communication with the vent path upon said selective opening of the valve rod; and wherein the valve rod is reciprocated by gas pressure within the valve conduit to slide against the bias, and provides an automatic selective opening for gas to pass from the vent path to the atmosphere based on the gas pressure, and wherein a vent path connector associated with the trocar assembly defines a first gas passageway to the venting valve assembly, and the valve conduit in fluid communication with the gas supply tube defines a separate second gas passageway from the venting valve assembly, such that the gas from the trocar assembly passes from the vent path to atmosphere by selective gas pressure actuation of the valve rod.

5. The improved tissue sealant spray applicator of claim 4, wherein the elongate delivery tube further includes a third gas passageway in fluid communication with the adapter member outlet of the spray adapter member, the third gas passageway of the elongate delivery tube having a separate passageway for each component of the multi-component tissue sealant, and the third gas passageway and the separate passageway for each component of the multi-component tissue sealant terminating at the distal end region of the elongate delivery tube at a ring member having a plurality of teeth projecting radially inwardly from an inner diameter of the ring, the teeth extending across an outlet end of the third gas passageway and around an outer wall of the separate passageway, whereby the outer wall of the separate passageway, the teeth, and the inner diameter of the ring member define a plurality of apertures in the distal end region of the elongate delivery tube.

\* \* \* \* \*